United States Patent [19]

Walker et al.

[11] Patent Number: 5,571,910

[45] Date of Patent: Nov. 5, 1996

[54] PROCESS FOR THE PREPARATION OF INTERMEDIATES USEFUL IN THE SYNTHESIS OF CEPHALOSPORINS

[75] Inventors: Derek Walker, Summit; Junning Lee, Gillette, both of N.J.; Charles R. Martin; Haiyan Zhang, both of Fort Collins, Colo.; Loris Sogli, Novara; Ermanno Bernasconi, Caronno Varesino, both of Italy

[73] Assignee: Schering Corporation, Kenilworth, N.J.

[21] Appl. No.: 451,287

[22] Filed: May 26, 1995

Related U.S. Application Data

[63] Continuation of Ser. No. 353,030, Dec. 9, 1994, abandoned.

[51] Int. Cl.⁶ .................................................. C07D 501/22
[52] U.S. Cl. .......................................... 540/230; 540/215
[58] Field of Search ..................................... 540/222, 215, 540/221, 230

[56] References Cited

U.S. PATENT DOCUMENTS

| | | | |
|---|---|---|---|
| 3,792,995 | 2/1974 | Ochiai et al. | 204/72 |
| 4,008,228 | 2/1977 | Chauvette | 260/243 |
| 4,042,472 | 8/1977 | Hall | 204/73 |
| 4,379,739 | 4/1983 | Hall | 204/72 |
| 4,634,697 | 1/1987 | Hamashima | 514/202 |
| 5,126,446 | 6/1992 | Brown et al. | 540/230 |

FOREIGN PATENT DOCUMENTS

| | | |
|---|---|---|
| 0082656 | 6/1983 | European Pat. Off. . |
| 0359540 | 3/1990 | European Pat. Off. . |
| 0556630 | 8/1993 | European Pat. Off. . |

OTHER PUBLICATIONS

Yoshioka, *Pure Appl. Chem.*, 59, 1041–1046 (1987).
Jones, et al., *J. Pharm. Pharmac.*, 20 (Suppl.) 45S–47S (1968).
Hall, *J. Pharm. Sci.*, 62, (6) 980–983 (1973).
Ochiai et al., *J. Chem. Soc., Perkin Trans. 1*, 258–262 (1974).
Baldwin, et al., *Tetrahedron*, 49, (22) 4907–4922 (1993).
Torii, et al., *Bull. Chem. So. Jpn.*, 59 3975–3976 (1986).
Torii, et al., *Bull. Soc. Chim. Belg.*, 91 (12) 951–965 (1982).
Hamashima, et al., *J. Antiobiot.*, 40, (10) 1468–1470 (1987).
Ochiai, et al., *Tet. Lett.*, (23) 2341–2344 (1972).
Hall, et al., *J. Electranal. Chem.*, 80 155–170 (1977).
"Kirk–Othmer Concise Encyclopedia of Chemical Technology", John Wiley & Sons, New York, 843–844 (1985).

*Primary Examiner*—John M Ford
*Attorney, Agent, or Firm*—Paul A. Thompson; John H. C. Blasdale; Norman C. Dulak

[57] ABSTRACT

A process is described for preparing 3-exomethylene cephalosporanic acid derivatives for use in the synthesis of cephalosporin antibiotics such as ceftibuten. The process comprises electrochemical reduction of a compound of the formula (IV)

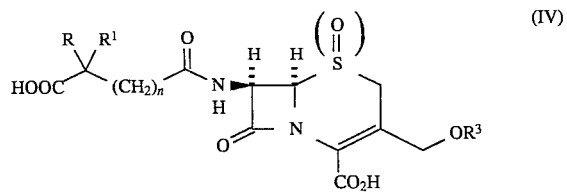

wherein: $R^3$ is $CH_3C(O)$—;

$$\left(\begin{array}{c} O \\ \| \\ S \end{array}\right)$$

is an optional sulfoxide group; n is 2 or 3; $R^1$ is H and R is H or $NHR^2$, where $R^2$ is H or a protecting group selected from $C_6H_5CH_2OC(O)$—, $C_6H_5C(O)$— or $C_1$–$C_6$ alkoxy—$C(O)$—; or wherein R and $R^1$ together with the carbon atom to which they are attached comprise —C(O)—, and produces the desired 3-exomethylene compounds with low levels of the corresponding 3-methyl tautomers.

2 Claims, No Drawings

PROCESS FOR THE PREPARATION OF INTERMEDIATES USEFUL IN THE SYNTHESIS OF CEPHALOSPORINS

This is a continuation of application Ser. No. 08/353,030, filed Dec. 9, 1994, now abandoned.

The present invention provides a process for preparing intermediates useful in the synthesis of cephalosporin type antibiotics.

BACKGROUND OF THE INVENTION

U.S. Pat. No. 4,634,697 describes cephalosporin compounds including Ceftibuten, a commercially important third generation cephalosporin type antibiotic having the chemical formula (I)

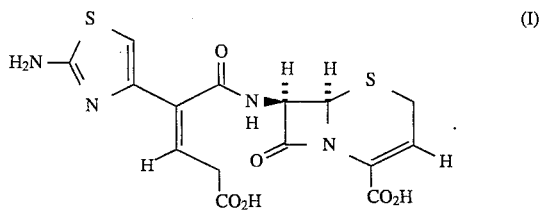

The synthesis of ceftibuten starting from penicillin G is described in Yoshioka, *Pure Appl. Chem.*, 59, 1041 (1987). However, this process is costly and inefficient leaving a current need for a more cost effective and efficient process for the commercial scale preparation of ceftibuten.

The electrochemical transformation of derivatives of cephalosporin C is known. See, Jones, et al., *J. Pharm. Pharmac.*, 20, (Suppl.) 45S–47S (1968), and Hall, *J. Pharm. Sci.*, 62, (6) 980–983 (1973). The formation of 3-exomethylene cephalosporins via eletrochemical reduction is described in Ochiai, et al., *J. Chem. Soc., Perkin Trans. I*, 258–262 (1974) and U.S. Pat. Nos. 3,792,995 and 4,042,472. Baldwin, et al., *Tetrahedron*, 49, (22) 4907–4922 (1993), also describes the electrochemical reduction of cephalosporin C to form an 3-exomethylene compound of the formula

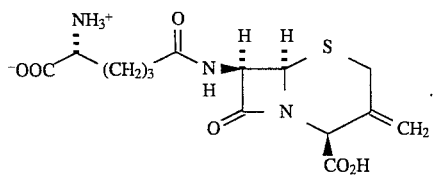

In addition, EP 082,656 describes the electrochemical reduction of acetoxymethyl compounds of the formula

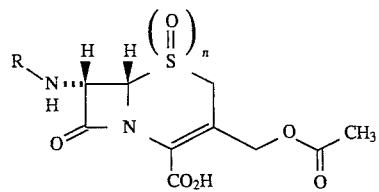

wherein n is 0 or 1, and R is H or an acyl group, to form the corresponding 3-exomethylene compounds.

The eletrochemical processes described above are chemically inefficient, providing low yields and producing significant levels of the 3-methyl tautomer of the desired 3-exomethylene compounds. These 3-methyl compounds are essentially useless for the synthesis of cephalosporin type antibiotics and are difficult to remove from the desired 3-exomethylene product. As a result, 3-exomethylene compounds prepared via the prior art the prior art electrochemical processes are unsuitable for use in the manufacture of cephalosporin drugs. Consequently, in spite of the potential advantages of these electrochemical processes, such as environmental cleanliness and safety, not one has been developed into a commercial scale process. There is therefore a need for an electrochemical process which will produce 3-exomethylene cephalosporins in high yield and with low levels (i.e., less than 10%) of 3-methyl tautomers.

SUMMARY OF THE INVENTION

The present invention provides an electrochemical process for preparing 3-exomethylene cephalosporins while producing low levels of the 3-methyl tautomer. More specifically the present invention provides a process for preparing compounds of the formula (II) or (III) and esters thereof

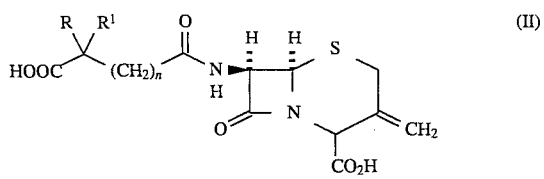

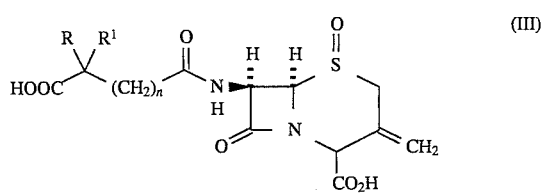

wherein: n is 2 or 3; $R^1$ is H and R is H or $NHR^2$, where $R^2$ is H or a protecting group selected from $C_6H_5CH_2OC(O)-$, $C_6H_5C(O)-$ or $C_1-C_6$ alkoxy—$C(O)-$; or wherein R and $R^1$ together with the carbon atom to which they are attached comprise —C(O)—. Compounds (II) and (III) and the esters thereof are useful as intermediates in the synthesis of ceftibuten (I).

The process of the present invention comprises ectrochemically reducing a compound of the formula (IV)

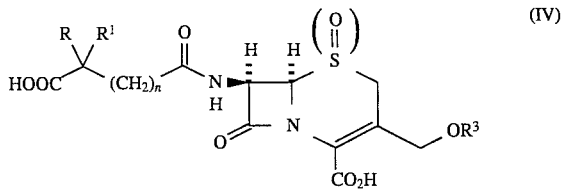

wherein: $R^3$ is $CH_3C(O)-$;

$$\begin{pmatrix} O \\ \| \\ \end{pmatrix}$$

is an optional sulfoxide group; and n, R and $R^1$ are as defined above, in the presence of a buffer and a solvent selected from water, an organic solvent, or a mixture of water and a water miscible organic additive, to form a compound of the formula (II) or (III).

The present invention also provides novel compounds of the formula (II) or (III) as defined above, wherein n is 2 or 3; $R^1$ is H and R is H or $NHR^2$, where $R^2$ is $C_6H_5C(O)-$; $C_6H_5CH_2OC(O)-$, or $(CH_3)_2CHCH_2OC(O)-$; or wherein R and $R^1$ together with the carbon to which they are attached comprise —C(O)—, and esters or salts thereof.

In an alternative embodiment, the present invention provides a process for preparing compounds of the formula (V)

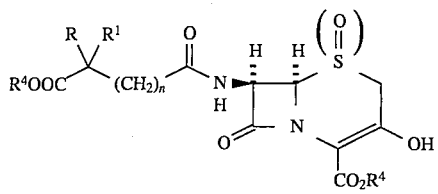
(V)

wherein $R^4$ is diphenylmethyl, and n,

R and $R^1$ are as defined above. In this embodiment the process of the present invention comprises:

(a) electrochemically reducing a compound of the formula (IV), as defined above, to form a compound of the formula (II) or (III), as defined above;

(b) esterifying the compound of formula (II) or (III) from step (a) to form a compound of the formula (VI)

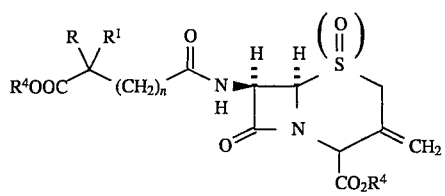
(VI)

wherein $R^4$ is diphenylmethyl, and n,

R and $R^1$ are as defined above; and (c) ozonolyzing the compound (VI) from step (b) to form a compound of the formula (V), as defined above.

The present invention further provides a process for preparing the diphenylmethyl ester of 7-amino-3-desacetoxymethylcephalosporanic acid, i.e., a compound of the formula (VII)

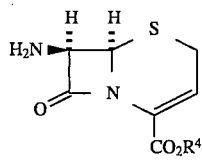
(VII)

wherein $R^4$ is diphenylmethyl, comprising the steps:

(d) reducing a compound of the formula (V) as defined above to form a compound of the formula (VIII)

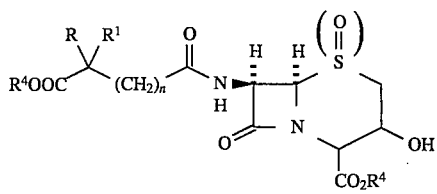
(VIII)

wherein $R^4$, n, R,

and $R^1$ are as defined above;

(e) reacting the product of step (d) with a compound of the formula P–X, wherein P is a sulfonyl activating group and X is Cl, Br or I, in the presence of a tertiary amine base to form a compound of the formula (IX)

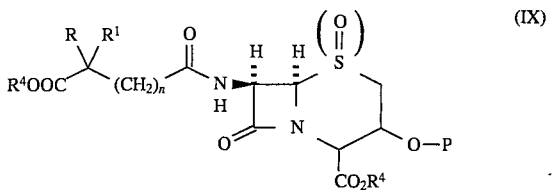
(IX)

wherein P is a sulfonyl activating group, and $R^4$, n,

R and $R^1$ are as defined above; and (f) (i) treating the product of step (e) with $PCl_5$ in the presence of a tertiary amine base and an alcohol or diol, then with a dialkylamine base; or (ii) treating the product of step (e) with a dialkylamine base or a tertiary amine base, and then with $PCl_5$ in the presence of a tertiary amine base and an alcohol or diol; and where an optional

group is present treating with $PCl_3$; to form a compound of the formula (VII). Compound (VII) is a key intermediate in the commercial synthesis of ceftibuten (I).

DETAILED DESCRIPTION

As used herein, the term:

"alkyl" means a straight or branched alkyl chains of 1 to 6 carbon atoms;

"aryl" means a $C_6$–$C_{10}$ carbocyclic aromatic group, such as phenyl or naphthyl; and "substituted aryl" means an aryl group having 1 to 3 substituents selected from halogeno, $C_1$–$C_6$ alkyl, $NO_2$ or $CF_3$;

"halogeno" means Cl, Br or I;

"sulfonyl activating group" means a substituent of the formula —$SO_2R^6$, wherein $R^6$ is $C_1$–$C_6$ alkyl, aryl, substituted aryl or —$CF_3$;

"hydride reducing agent" means NaBH4, $LiBH_4$, $NaBH_3CN$, or a combination of $NaBH_4$ and LiCl;

"aqueous acid" means an aqueous solution of an acid, such as HCl;

"dialkylamine base" means a compound of the formula $HN(alkyl)_2$, such as diethylamine;

"tertiary amine base" means bases such as pyridine, DMAP, DMA, $Et_3N$ or Hünigs base;

"tetra(alkyl)ammonium salts" mean salts comprising a tetra(alkyl)ammonium cation, such as tetraethylammonium, tetramethylammonium, tetrabutylammonium or tetrapropylammonium, and a suitable counterion such as p-toulenesulfonate or sulfate;

"alcohol" means a $C_1$-$C_4$ alcohol, such as methanol, ethanol or i-propanol; and "diol" means a $C_3$-$C_6$ diol, such as 1,3-propanediol or 1,3-butanediol.

"Buffer" means one or more buffer compounds which are water soluble acids and/or bases, such as $KH_2PO_4$, $NaH_2PO_4$, $K_2HPO_4$, $Na_2HPO_4$, $K_3PO_4$, $Na_3PO_4$, $NaHCO_3$, $KHCO_3$, $Na_2CO_3$, $K_2CO_3$, $Li_2CO_3$, NaOH, KOH, LiOH and $H_3BO_3$, or salts, including borates and quaternary ammonium salts, such as tetra(alkyl)ammonium salts. The buffer is an individual buffer compound, or two or more such compounds in combination, and is used to maintain constant pH during the course of the eletrochemical reduction.

"Water miscible organic additives" are organic compounds which are soluble in water and relatively unsusceptible to electrochemical reduction under the conditions of the present invention, such as EtOAc, iPrOAc, $CH_3CN$, MeOH, EtOH, iPrOH, DMF, formamide, DMSO or urea.

As used herein the following reagents and solvents are identified by the abbreviations indicated: methanol (MeOH); tetrahydrofuran (THF); diethyl ether ($Et_2O$); t-butyl methyl ether (TBME); triethylamine ($Et_3N$); di-isopropylethylamine (Hünigs base); ethyl acetate (EtOAc); iso-propylacetate (iPrOAc); ethanol (EtOH); N,N-dimethylformamide (DMF); dimethylsulfoxide (DMSO); 4-dimethylaminopyridine (DMAP); N,N-dimethylaniline (DMA); p-toluenesulfonyl chloride (tosyl chloride or TsCl); methanesulfonyl chloride (mesyl chloride or MsCl); p-toluenesulfonic acid (p-TSA); iso-propanol (iPrOH).

The present invention comprises a process for preparing a compound of the formula (II) or (III) as shown in Reaction Scheme 1.

Reaction Scheme 1

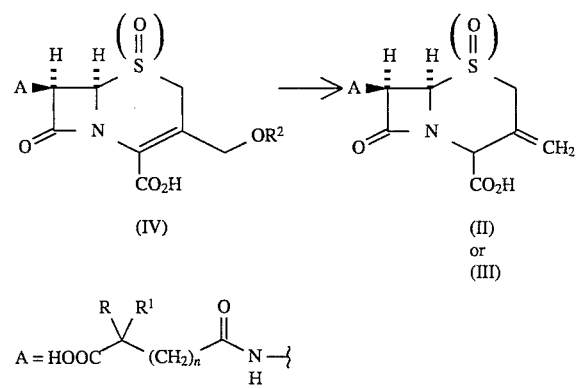

(IV) → (II) or (III)

$A = HOOC\underset{(CH_2)_n}{\overset{R\ R^1}{\diagdown\diagup}}\overset{O}{\underset{H}{\overset{\|}{C}-N-\}}}$ In Reaction Scheme 1, a solution comprising a compound of the formula (IV), as defined above, a suitable solvent, and a buffer, is electrochemically reduced. The working electrode (cathode) for this reduction is selected from known electrode materials, such as carbon, lead, platinum, mercury or zinc electrodes, with mercury or zinc being most preferred. Preferably the cathode has a high surface area such that the ratio of electrode area to solution volume is optimized. The potential of the electrode during the electrochemical reduction is held at about −1 to −3 volts vs. a saturated calomel electrode, to form a compound of the formula (II) or (III) as defined above. The solvent is selected from water, a suitable organic solvent, or a mixture of water and a water miscible organic additive, and is preferably water or a mixture of water and a water miscible organic additive.

The electrochemical reduction is carried out at a temperature of −60° to 80° C., preferably at −40° to 0° C., at a pH of 4 to 12, preferably at a pH 6 to 11, and most preferably at a pH of 7–10. A buffer, or a combination of two or more buffers, is used as needed to maintain the desired pH range.

The electrochemical reduction is carried out in a suitable electrochemical cell, a large variety of which are known in the art. Preferably the cell is a flow cell wherein the solution comprising the compound to be reduced is circulated through the electrochemical cell from an external reservoir. Also preferred is a two-chambered cell wherein the cathode and anode are contained in separate chambers. The cathode and anode chambers of such cells are constructed such that fluid contained in one chamber is physically separated from the other chamber by a suitable divider while maintaining an electrical connection between the chambers. Preferably the divider is a porous material, such as sintered glass, or a suitable ion exchange membrane, such as a Nafion® membrane.

Compounds of the formula (II), (III) and (IV) contain two carboxylic acid groups and therefore exist as anionic species at the preferred pH used for the electrochemical reduction. An ion exchange membrane divider, which is permeable to cations but not anions, can therefore be used to prevent migration of compounds (II), (III) and (IV) to the anode, thereby preventing the possibility of side reactions from occurring at that electrode. Preferably the ion exchange membrane is a perfluorinated ionomer membrane, such as the perfluorinated sulfonic acid or perfluorinated carboxylic acid ionomers described in the "Kirk-Othmer Concise Encyclopedia of Chemical Technology", John Wiley & Sons, p. 843–844 (New York, 1985), herein incorporated by reference. Most preferred are Nation® or Flemion® membranes, with Nation® membranes being especially preferred.

Compounds of the formula (IV) are known and can be readily prepared via established methods.

The present invention also provides a process for preparing compounds of the formula (V) as shown in Reaction Scheme 2.

Reaction Scheme 2

Step A

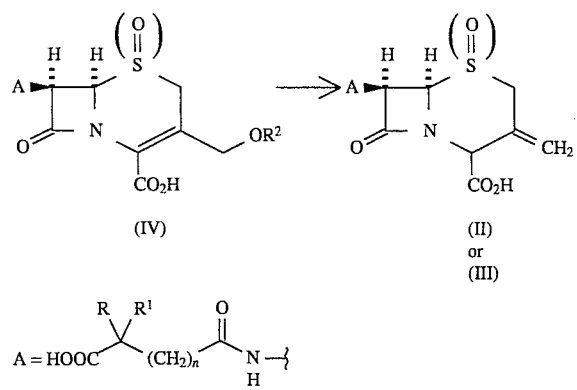

(IV) → (II) or (III)

$A = HOOC\underset{(CH_2)_n}{\overset{R\ R^1}{\diagdown\diagup}}\overset{O}{\underset{H}{\overset{\|}{C}-N-\}}}$ Reaction Scheme 2
-continued Step B (II) or (III) ⟶ 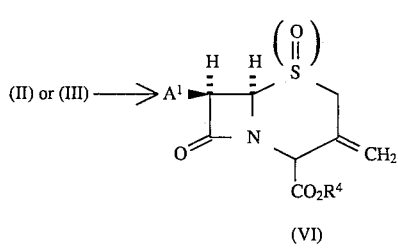

(VI)

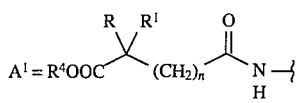

Step C (VI) —ozone→ 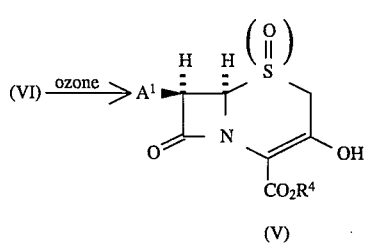

(V)

In Step A of Reaction Scheme 2 the starting compound (IV), as defined above, is eletrochemically reduced to a compound of the formula (II) or (III) via the same procedure described for Reaction Scheme 1.

In Step B, a compound of the formula (II) or (III) is esterified by treating with a suitable esterifying agent, such as diphenyldiazomethane, in a suitable solvent, such as water or a mixture of water and a polar organic solvent, to form the diester (VI), as defined above.

In Step C, the diester (VI) is treated with ozone in a suitable solvent, such as $CH_2Cl_2$, at a temperature of $-100°$ C. to $0°$ C., preferably at $-80°$ to $-20°$ C., to form an ozonide intermediate, then further treated with a suitable reducing agent, such as $P(OC_2H_3)_3$ to reduce the ozonide intermediate and form a compound of the formula (V), as defined above.

In an alternative embodiment, the product (II) or (III) of Step A is treated with ozone, using essentially the same procedure as described for Step C (above), to form a compound of the formula (X)

(II) or (III) —ozone→ 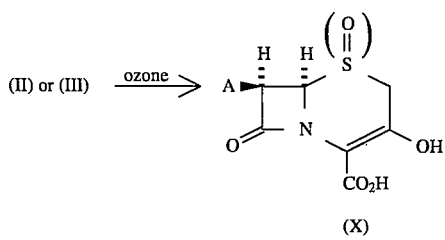

(X)

wherein A is as defined above, and the product (X) esterified using essentially the same procedure as described for Step B (above) to form a compound of the formula (V), as defined above.

The present invention further provides a process for preparing compounds of the formula (VII) as shown in Reaction Scheme 3.

Reaction Scheme 3

Step D

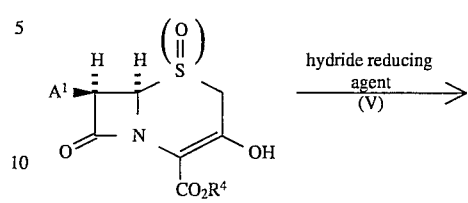

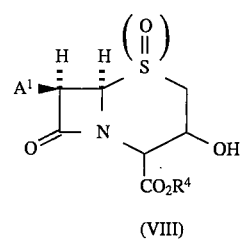

(VIII)

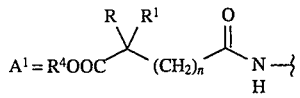

Step E (VIII) —P—X, tertiary amine base→ 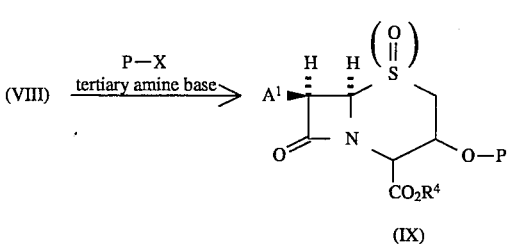

(IX)

Step F (IX) ⟶ 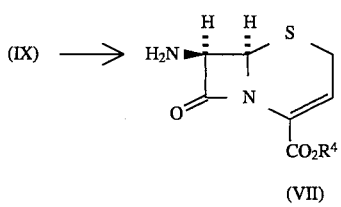

(VII)

Reaction Scheme 3, step D, a compound of the formula (V), as defined above, Is treated with a hydride reducing agent, preferably $NaBH_4$, in the presence of a suitable solvent to form a compound of the formula (VIII), wherein n, R, $R^1$, $R^4$ and

are as defined above. Suitable solvents include $Et_2O$, THF, a $C_1$–$C_4$ alcohol, water, a mixture of $CH_2Cl_2$ and a $C_1$–$C_4$ alcohol, or a mixture of water and a $C_1$–$C_4$ alcohol. The reaction is carried out at a temperature of $-100°$ C. to $30°$ C., preferably at $-80°$ C. to $0°$ C., and the specific solvent or solvent mixture to be used is selected such that the reaction temperature is higher than the freezing point of the mixture. Preferably the solvent is a mixture of $CH_2Cl_2$ and a $C_1$–$C_4$ alcohol and the reaction temperature is $-80°$ to '$40°$ C.

Steps E and F of Reaction Scheme 3 are carried out as a "one pot" process, i.e., the required reagents are sequentially added to the reaction mixture without workup or isolation between steps.

In Step E, the product (VIII) of step D is reacted with a compound of the formula P–X, wherein P and X are as defined above, in a suitable solvent, such as $CH_2Cl_2$, in the presence of a tertiary amine base, such as $Et_3N$, to form a mixture comprising a compound of the formula (IX), wherein P, $R^3$, n,

R and $R^1$ are as defined above, and a tertiary amine base.

In step F, the product mixture from step E is treated sequentially with $PCl_5$ and a dialkylamine base, such as diethylamine, to form a compound of formula (VII). Treatment with $PCl_5$ in the presence of the tertiary amine base and a $C_1$–$C_4$ alcohol, preferably methanol, or a $C_3$–$C_6$ diol, preferably 1,3-butanediol, serves to cleave the amide side chain to form the free amino group. Additional tertiary amine base is added with the $PCl_5$ in step F as necessary. Treatment with dialkylamine base results in elimination of the 3-OP group to form the 3,4 double bond.

The reaction is carried out by adding $PCl_5$ and an alcohol or diol to the mixture, followed by treatment with a dialkylamine base. Alternatively the mixture is first treated with the dialkylamine base followed by treatment with $PCl_5$ and alcohol or diol.

Where an optional

group is present, step F further comprises treatment with $PCl_3$ to reduce the sulfoxide group to the analogous sulfide.

Compounds of the formula (VII) are readily converted to ceftibuten (I) via known methods.

In an alternative embodiment, the product (X) described above is treated with a hydride reducing agent, using essentially the same procedure as described for Step D (above) to form a compound of the formula (XI)

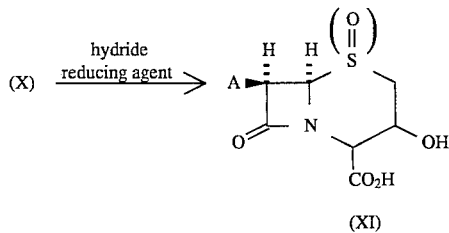

wherein A is as defined above, and the compound (XI) esterified via essentially the same procedure as described in Step B of Reaction Scheme 2 (above) to form a compound of the formula VIII), as defined above. The compound VIII) is then converted to a compound of the formula VII) via the procedures described for Steps E and F (above).

The following preparations and examples are illustrative of the process of the present invention.

EXAMPLES

Materials and General Methods:

Electrochemical reductions are carried out in an electrochemical cell with the counter electrode (anode) separated from the working (cathode) and reference electrodes. The potential is controlled using a constant voltage source, such as a Princeton Applied Research Model 273 potentiostat, at from –1 to –3 volts, preferably from –1.5 to –2.5 volts.

Nafion® membranes for use as dividers are commercially available from a number of sources, e.g. DuPont or Aldrich Chemical Company. The Nafion® membrane is cleaned prior to use by boiling in 3% $H_2O_2$ for 30 minutes, followed by immersion in a hot (80° C.) solution of 9M nitric acid for 15 minutes. The membrane is then rinsed in boiling water, sonicated in several aliquots of hot (90° C.) water and stored under distilled water until needed.

The counter electrode is a platinum mesh electrode and the reference electrode is an Ag/AgCl electrode. The working electrode is a mercury pool (triple-distilled mercury) electrode; graphite (Johnson Mathey, 99.9995%) electrode; glassy carbon electrode, lead (Johnson Mathey 99.9999%) electrode or zinc (Johnson Mathey, 99.95%) rod sealed in Teflon®.

HPLC analysis is performed on a Brownlee HPLC Analytical Column (RP 18 SPHER I-5, 250 X 4.6 mm) maintained at a temperature of 35° C. The mobile phase is 94:6 0.025M $K_2HPO_4$ (aqueous)/$CH_3CN$, and a UV detector is used.

Example 1

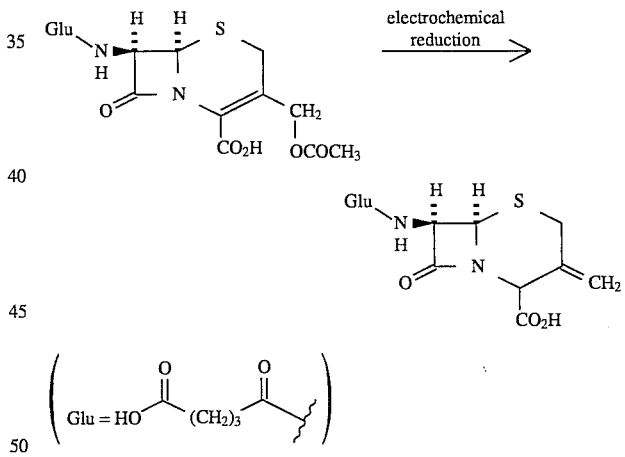

Dissolve 0.3 g of 7-glutaroyl 7-aminocephalosporanic acid in 30 mL of a pH 6.9 aqueous buffer solution of 0.1M $KH_2PO_4$, 0.1M $Na_2HPO_4$ and 0.018M $NaHCO_3$. Eletrolyze the solution at room temperature using a mercury pool working electrode at a potential of –2.2 V for a period of 13 hours to give a 8.5:1 mixture of the exomethylene product and a 3-methyl compound of the formula

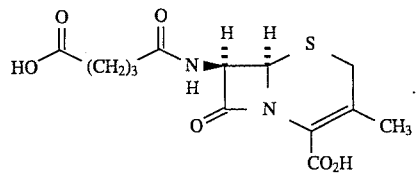

Example 1A

Dissolve 0.3 g of 7-glutaroyl 7-aminocephalosporanic acid in 30 mL of an aqueous buffer solution of 1M $H_3BO_3$ and add NaOH to adjust to pH 8.0. Eletrolyze as described for Example 1 at a potential of −2.3 V for a period of 4 ¾ hours to give a 6.8:1 mixture of the same compounds as for Example 1.

Example 2

Prepare an aqueous electrolysis solution of 7-glutaroyl 7-aminocephalosporanic acid (glutaroyl 7-ACA); 0.05M $KH_2PO_4$; 0.05M $Na_2HPO_4$; 0.08M boric acid; and 0.018M $NaHCO_3$. Record the initial pH of the solution and electrolyze as described for Example 1 at a potential of −2.2 V. Record the final pH and analyze by HPLC, as described above, to determine the yield and the ratio of 3-exomethylene to 3-methyl compound in the product mixture. Using the starting concentration of 7-glutaroylcephalosporanic acid indicated, the following results are obtained:

| Concentration of glutaroyl 7-ACA | Yield of exomethylene product | pH initial | pH final | Ratio 3-exo/3-methyl |
|---|---|---|---|---|
| 1 g/L | 52% | 7.3 | 8.5 | 9.5:1 |
| 5 g/L | 50% | 6.8 | 8.9 | 10.1:1 |
| 10 g/L | 43% | 6.3 | 8.5 | 10.6:1 |

Example 3

Prepare an aqueous electrolysis solution of 5 g/L of 7-glutaroyl 7-aminocephalosporanic acid (glutaroyl 7-ACA) and 0.2M boric acid. Add NaOH to adjust the initial pH of the solution. Using a 2-chambered cell separated by a divider, electrolyze the solution as described for Example 1 at a potential of −2.2 V. Record the final pH and analyze by HPLC, as described above, to determine the yield and the ratio of 3-exomethylene to 3-methyl compound in the product mixture. At the reaction temperature indicated, the following results are obtained:

| Reaction Temp. | Divider material | Yield of exomethylene product | pH initial | pH final | Ratio 3-exo/3-methyl |
|---|---|---|---|---|---|
| 25° C. | sintered glass | 49% | 8.3 | 9.4 | 10.4:1 |
| 25° C. | Nafion ® | 64% | 8.3 | 9.3 | 10.6:1 |
| 0° C. | Nafion ® | 67% | 8.7 | 8.3 | 13.5:1 |

We claim:
1. A compound of the formula

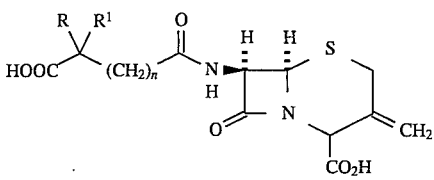

wherein: n is 2 or 3;; $R^1$ is H and R is H or $NHR^2$, where $R^2$ is $C_6H_5C(O)-$; $C_6H_5CH_2OC(O)-$, or $(CH_3)_2CHCH_2OC(O)-$; or wherein R and $R^1$ together with the carbon to which they are attached comprise $-C(O)-$;

and salts thereof.

2. A compound having the structural formula

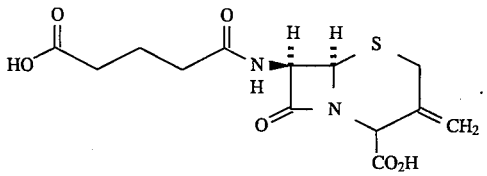

* * * * *

UNITED STATES PATENT AND TRADEMARK OFFICE
CERTIFICATE OF CORRECTION

PATENT NO. : 5,571,910
DATED : November 5, 1996
INVENTOR(S) : Derek Walker et al It is certified that error appears in the above-indentified patent and that said Letters Patent is hereby corrected as shown below:

On the title page: Item [73] Assignee should read

--Schering Corporation, Kenilworth, N.J. and Antibioticos, Milan, Italy--

Signed and Sealed this

Fourteenth Day of October, 1997

*Attest:*

BRUCE LEHMAN

*Attesting Officer*        *Commissioner of Patents and Trademarks*